(12) United States Patent
Azzazy et al.

(10) Patent No.: US 8,264,689 B1
(45) Date of Patent: Sep. 11, 2012

(54) MICRO GAS CELL ARRAY DEVICE AND METHOD

(75) Inventors: Medhat Azzazy, Laguna Niguel, CA (US); Ying Hsu, San Clemente, CA (US); John C. Carson, Corona del Mar, CA (US)

(73) Assignee: ISC8 Inc., Costa Mesa, CA (US)

( * ) Notice: Subject to any disclaimer, the term of this patent is extended or adjusted under 35 U.S.C. 154(b) by 306 days.

(21) Appl. No.: 12/653,730

(22) Filed: Dec. 17, 2009

Related U.S. Application Data

(60) Provisional application No. 61/203,276, filed on Dec. 22, 2008.

(51) Int. Cl.
*G01N 21/00* (2006.01)

(52) U.S. Cl. ...................................................... 356/437

(58) Field of Classification Search .................. 356/432, 356/437, 439, 440
See application file for complete search history.

(56) References Cited

U.S. PATENT DOCUMENTS

| | | | | |
|---|---|---|---|---|
| 3,805,074 | A * | 4/1974 | McCormack | 250/354.1 |
| 4,543,486 | A * | 9/1985 | Rose | 250/492.1 |
| 5,317,156 | A * | 5/1994 | Cooper et al. | 250/345 |
| 5,418,366 | A * | 5/1995 | Rubin et al. | 250/338.5 |
| 5,479,019 | A * | 12/1995 | Gross | 250/345 |
| 5,930,000 | A * | 7/1999 | Brand | 356/437 |
| 6,791,086 | B2 * | 9/2004 | Russell | 250/339.07 |
| 6,977,722 | B2 * | 12/2005 | Wohlstadter et al. | 356/246 |
| 7,064,835 | B2 * | 6/2006 | Riley et al. | 356/437 |
| 7,146,857 | B2 | 12/2006 | Hok | |
| 7,157,711 | B1 * | 1/2007 | Russell | 250/339.07 |
| 7,427,501 | B2 * | 9/2008 | Bachur et al. | 435/287.3 |
| 7,502,109 | B2 | 3/2009 | Bonne et al. | |
| 7,605,370 | B2 | 10/2009 | Russell | |
| 7,606,274 | B2 | 10/2009 | Mirov et al. | |
| 7,884,937 | B2 * | 2/2011 | Prasad et al. | 356/437 |
| 2005/0046851 | A1 * | 3/2005 | Riley et al. | 356/437 |
| 2007/0164221 | A1 * | 7/2007 | Russell | 250/339.07 |
| 2008/0259340 | A1 * | 10/2008 | Prasad et al. | 356/437 |

* cited by examiner

*Primary Examiner* — Roy M Punnoose
(74) *Attorney, Agent, or Firm* — W. Eric Boyd, Esq.

(57) ABSTRACT

A device and method for the detection of one or more gases is disclosed.

A MEMS structure comprising a micro gas cell array is provided comprising one or more micro gas cells having a predetermined gas therein. The micro gas cells define an optical path therethrough and may comprise a micro lens. Electromagnetic energy from a scene is collected and passed through one or more micro gas cells whereby electromagnetic energy emitted or reflected from a gas of interest in a scene is absorbed by a substantially identical gas contained within a micro gas cell. In this manner, the micro gas cell acts as a spectral filter.

The electromagnetic outputs of the micro gas cells, which may comprise one or more spectrally inert micro gas cells, are received by one or more detector elements such as a photon detector array. The ratio of the outputs of the related detector elements are computed by processing electronics, resulting in the identification of the gas of interest.

17 Claims, 3 Drawing Sheets

MICRO GAS CELL ARRAY DEVICE AND METHOD

CROSS-REFERENCE TO RELATED APPLICATIONS

This application claims the benefit of U.S. provisional patent application No. 61/203,276, filed on Dec. 22, 2008 entitled "Micro Gas Cell Array Device and Method Comprising Remote Optical Respiration Rate Function" pursuant to 35 USC 119, to which priority is claimed and which application is incorporated fully herein by reference.

STATEMENT REGARDING FEDERALLY SPONSORED RESEARCH AND DEVELOPMENT

N/A

DESCRIPTION

1. Field of the Invention

The invention relates generally to the field of gas detection systems. More specifically, the invention relates to a multi-spectral gas detection sensor system having a micro gas cell array for the detection a plurality of gases having different energy absorption bands.

2. Background of the Invention

There exists a need for a portable or hand-held sensor capable of detecting a range of hazardous gas conditions in, for instance, military, industrial or search and rescue applications. Such hazardous conditions include the presence of chemical, biological, radioactive, nuclear and/or explosive (CBRNE) elements and atmospheric gases that pose threats to individuals who are or may be potentially exposed to such conditions.

Existing devices used for detection of these gas elements are cumbersome to use, difficult to transport and have limited capabilities. What is needed is a small and multi-functional sensor device that can be packaged to form a hand-held system. Such a device is desirably capable of measuring a variety and range of different chemical and air quality hazards with high reliability.

The capability for detecting a wide range of gas elements with a near zero false negative detection rate in a hand-held instrument is not presently available with current state of art gas sensor technology.

Presently, remote optical gas detection systems exist for measuring air quality, detecting certain gas elements and hydrocarbons and use infrared or UV detectors. Both active (with illumination) and passive gas detection systems have been used in oil refineries, chemical and waste processing plants and chemical storage facilities. These systems however are relatively large and are mounted on fixed platforms or tripods and with related camera equipment, weigh in the range of 12 to 30 pounds. These features undesirably limit the use of such systems and further, these systems are designed to detect a specific type of gas with a unique chemical signature and are not capable of detecting gas mixtures or different types of gases.

The micro gas cell array technology of the instant invention addresses the above deficiencies in the prior art remote gas sensing devices, offering multi spectral gas sensing, compact size and high reliability.

SUMMARY OF THE INVENTION

The instant invention takes advantage of established optical gas detection technology in combination with novel elements that enable the accurate detection of a user-selected variety of chemical or gas elements while allowing the overall sensor system size to remain relatively compact.

An important element of the disclosed invention is the use of an array of micro gas cells; each cell holding a user-selected sample of gas of interest, preferably under pressure. The individual micro gas cells essentially act as matched spectral filters that absorb (i.e., block out) spectral electromagnetic signals emitted (or reflected) by a gas "plume" in the scene of interest which comprises the same chemical element as that disposed in the micro gas cell.

By comparing the intensity of the electromagnetic energy (using photon detector elements) from a scene after it passes through a selected micro gas cell with the electromagnetic energy from the scene after passing through an empty (e.g., vacuum or spectrally neutral gas) cell, the concentration of the chemical elements in the gas plume scene can be closely estimated.

Further, using multiple detector output signals received from an array of micro gas cells having different gases disposed therein, the spectral "signatures" of individual gas chemical compounds as well as gas mixtures can be compared and determined.

The micro gas cell array sensor system of the invention may generally comprise collection optics, optical scanning means such as a miniature tilt/tip or scanning mirror system, beam splitting means for directing a first portion of the electromagnetic energy from a scene to a first micro gas cell and for directing a second portion of the electromagnetic energy from the scene to a second (e.g., reference cell) micro gas cell, a micro gas cell array such as a MEMS structure, a photon detector array having detector elements with a predetermined responsivity to a preselected range of the electromagnetic spectrum, and processing electronic circuitry for the processing of the output of the detector array signals.

The micro gas cell array may comprise one or more sealed gas volumes filled with one or more predetermined gases. One or more of the gases in the sealed volumes may be under a pressure greater than one atmosphere.

In cases where reference micro gas cells are desired, such cells may be either empty, have a partial vacuum or be filled with spectrally neutral gas. Redundant cells of identical gases may also be provided to allow multiple readings by the system.

In a MEMS-based micro gas cell array embodiment of the invention, the small size (millimeters) of the micro gas cells permits the containment of the predetermined gases under pressure with ample safety margin.

Generally, prior art optical gas detection systems are designed to identify the presence of a particular gas or a few similar gases. Prior art detection is generally performed using optical elements such as filters or diffraction gratings for isolating a particular spectrum corresponding to the absorption bands of the gas(es) of interest. To detect several types of gases using prior art devices, multiple filters or multi-spectral components are required, resulting in undesirably large and complex optical systems.

The instant invention beneficially simplifies the above prior art optical systems by, in a preferred embodiment, incorporating a simple and compact array of micro gas cells in combination with an array of detector elements.

Further, in prior art devices, the detection of a particular chemical compound is generally achieved by measuring the attenuation of the radiative signal after passing through the filter. Most gases, however, have multiple energy absorption bands; hence, a difficulty in designing these filters is the selection of an electromagnetic spectrum that is well-isolated from the energy absorption bands of other gases in the scene and in the atmosphere.

The identification of a specific gas in a mixture is therefore a particularly challenging task for single spectral filter systems. The micro gas cell array of the instant invention minimizes this difficulty by the use of an array of known and predetermined gases as matched spectral filters, thus providing the processing electronics and related algorithm with a large matrix of outputs for comparison with a database of gas absorption characteristics.

Yet further, a technical challenge in optical filter design is the ability of the selected filter to maintain its performance over changes in environmental conditions. For example, to overcome performance changes due to temperature, filter designs often incorporate compensation elements intended to cancel out the effect of the temperature on optical films or elements used in the system.

Prior art filter environmental compensation approaches for broad temperature and humidity conditions for a wide range of gases are difficult. A primary advantage of the use of micro gas cells as filtering elements is that the gas in the micro cell is substantially chemically identical to that of the gas of interest in the scene, thus both will respond and change in concert with changes in the environment.

The multi-spectral gas detection system of the invention provides a number of advantages over the prior art such as those set forth below.

A first advantage of the invention is the capability for search and rescue personnel to determine multiple threats simultaneously using a single instrument. An array of micro gas cells provides a large set of gaseous samples or hazardous chemicals making it easier to quickly and reliably identify hazardous compounds under unknown conditions.

A further advantage is fast scene analysis where a single instrument with a large number of micro gas cells reduces the time it takes to identify the gas of interest as compared to using systems requiring numerous sampling cycles and which must deduce the answer through a process of elimination.

A yet further advantage of the disclosed invention is that it provides a compact optical system design with relatively few components wherein the micro gas cell array of the invention takes advantage of very small MEMS features. The array size is dependent only on the number of gas samples to be included in the system. Smaller gas cells provide the ability to withstand higher gas cell pressure, thus increasing the sensitivity of the system.

Finally, the simplicity of the disclosed device and method using relatively few components makes the system mechanically robust and allows redundancy in the system.

The net result is a micro gas cell array device and method for identifying gases in a scene that are highly reliable, robust and capable of ensuring near zero false negative detection.

In a first aspect of the invention, a micro gas cell is disclosed comprising a structure having at least one sealed gas volume and having a predetermined gas disposed therein and defining an optical path therethrough.

In a second aspect of the invention, a micro gas cell array is disclosed comprising a structure having a plurality of sealed gas volumes wherein each of the sealed gas volumes has a predetermined gas disposed therein and defines an optical path therethrough.

In a third aspect of the invention, a micro gas cell array is disclosed wherein at least one of the predetermined gases is disposed within one of the sealed gas volumes at a pressure greater than one atmosphere.

In a fourth aspect of the invention, a micro gas cell array is disclosed wherein at least one of the sealed gas volumes comprises a spectrally inert gas therein.

In a fifth aspect of the invention, a micro cell gas array is disclosed wherein at least one of the sealed gas volumes comprises at least a partial vacuum therein.

In a sixth aspect of the invention, a micro gas cell array is disclosed wherein the predetermined gases in at least two of the sealed gas volumes are substantially identical.

In a seventh aspect of the invention, a micro gas cell array is disclosed further comprising a micro lens disposed along the optical path through at least one of the sealed gas volumes.

In an eighth aspect of the invention, a micro gas cell array is disclosed further comprising collection optics means, a detector element having an electronic output responsive to a predetermined range of the electromagnetic spectrum and processing electronics for the processing of an electronic output.

In a ninth aspect of the invention, a micro gas cell array is disclosed further comprising collection optics means, optical scanning means, a photon detector array comprising a plurality of detector elements each having an electronic output responsive to a predetermined range of the electromagnetic spectrum and processing electronics for the processing of an electronic output.

In a tenth aspect of the invention, a micro gas cell array is disclosed further comprising means for beam splitting such as beam splitting optics.

In an eleventh aspect of the invention, a micro gas cell array is disclosed wherein at least one of the predetermined gases therein comprises $CO_2$.

In a twelfth aspect of the invention, a micro gas cell array is disclosed wherein at least one of the predetermined gases therein comprises CO.

In a thirteenth aspect of the invention, a micro cell gas array is disclosed wherein at least one of the predetermined gases therein comprises $H_2S$.

In a fourteenth aspect of the invention, a micro gas cell array is disclosed wherein at least one of the predetermined gases therein comprises $N_2O$.

In a fifteenth aspect of the invention, a micro gas cell array is disclosed wherein at least one of the predetermined gases therein comprises SO2.

In a sixteenth aspect of the invention, a micro gas cell array is disclosed wherein at least one of the predetermined gases therein comprises a hydrocarbon material.

In a seventeenth aspect of the invention, a method for identifying a gas is disclosed comprised of the steps of collecting electromagnetic radiation emitted or reflected from a scene, directing at least a first portion of the collected electromagnetic radiation through a first micro gas cell having a predetermined gas disposed therein, directing at least a second portion of the electromagnetic radiation collected from the scene through a second micro gas cell, receiving the at least first portion of electromagnetic energy upon a first detector element having an output responsive to a predetermined electromagnetic spectrum to provide a first detector output, receiving the at least second portion of electromagnetic energy upon a second detector element having an output responsive to a predetermined electromagnetic spectrum to provide a second detector output and comparing the ratio of the first detector output to the second detector output.

The method may further comprise beam splitting means and/or tip tilt optical scanning means for the steps of splitting and scanning collected electromagnetic energy across the micro gas cell array.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE INVENTION

Figures 1, 1A:
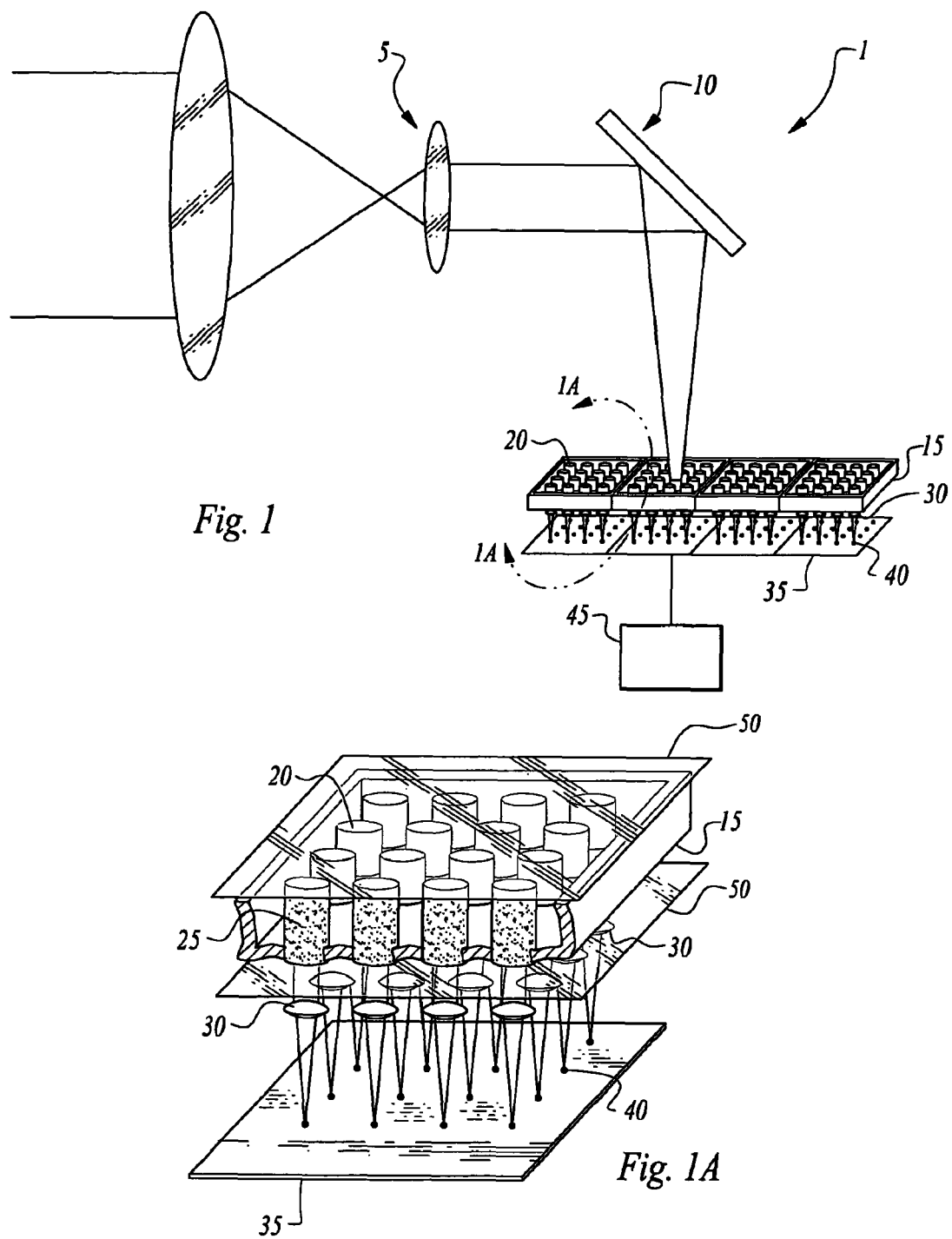
FIG. 1 is a block diagram of a preferred embodiment of the invention.
FIG. 1A is a break out of a portion of FIG. 1.

Turning now to the figures wherein like numerals designate like elements among the several views, a block diagram of a preferred embodiment the micro gas cell array sensor system 1 of invention is illustrated in FIGS. 1 and 1A.

A preferred embodiment of the micro gas cell array sensor system 1 may comprise collection optics means 5, optical scanning means such as tilt/tip mirror system 10 which may further comprise beam splitting optics means, a micro gas cell array 15 comprising one or more sealed cavities, one or more micro gas cells or sealed gas volumes 20 having a predetermined gas 25 disposed therein, one or more micro lens elements 30, a photon detector array 35 comprising one or more detector elements or pixels 40, and processing electronics 45.

As best seen in FIG. 1A, micro gas cell array 15 comprises one or more sealed gas volumes or micro gas cells 20 each filled with a predetermined, user selected gas 25.

Micro gas cells 20 are preferably sealed by means of a window material 50 on each terminal end of micro gas cells 20 wherein such window material 50 comprises a material that is substantially optically transparent to a predetermined portion of the electromagnetic spectrum.

Window material 50 is preferably selected whereby the desired electromagnetic energy from a scene passing through window material 50 is not substantially attenuated or distorted by the window material 50 itself and whereby sufficient electromagnetic energy is allowed to pass through the optical path defined by the micro gas cell 20 and to interact with gas 25 disposed therein and be subsequently received by detector elements 40 associated with the particular micro gas cells 20 to permit a useable output signal to be generated by photon detector array 35 for subsequent processing by processing electronics 45.

Micro gas cells 20 may further comprise one or more separate reference micro gas cells which reference cells may be empty, have a partial vacuum therein or may comprise a spectrally neutral gas.

In an alternative embodiment, redundant micro gas cells 20 comprising substantially identical gases may be provided to allow multiple, redundant readings by the system for enhanced accuracy.

The compact high reliability advantage of the disclosed invention is beneficially realized using micro-electro-mechanical systems technology (MEMS) for the manufacture of the micro gas cell array 15 structures.

Exemplar gases for use in the micro gas cells 20 may comprise gases with absorption spectra in the infrared region, such as, but not limited to $CO_2$, $N_2O$, CO, hydrocarbons, SO2, $H_2S$, and others.

The block diagram of FIG. 1 and FIG. 1A show the elements comprising the invention and the general operation of a preferred embodiment of the invention.

Collected radiation from the scene is collimated into a beam using suitable collection optics 5 and then directed towards the micro gas cell array 15 of micro gas cells 20. In a preferred embodiment, the diameter of micro gas cells 20 is about two mm. arranged in an array with about a four mm. pitch.

An array of micro-lenses 30 is preferably disposed proximal the output of the micro gas cells whereby micro-lenses 30 focus the collected radiation upon at least one detector element 40 of detector array 35. It is noted that the collected radiation may be focused upon more than one detector element 40 of photon detector array 35.

Figure 2:
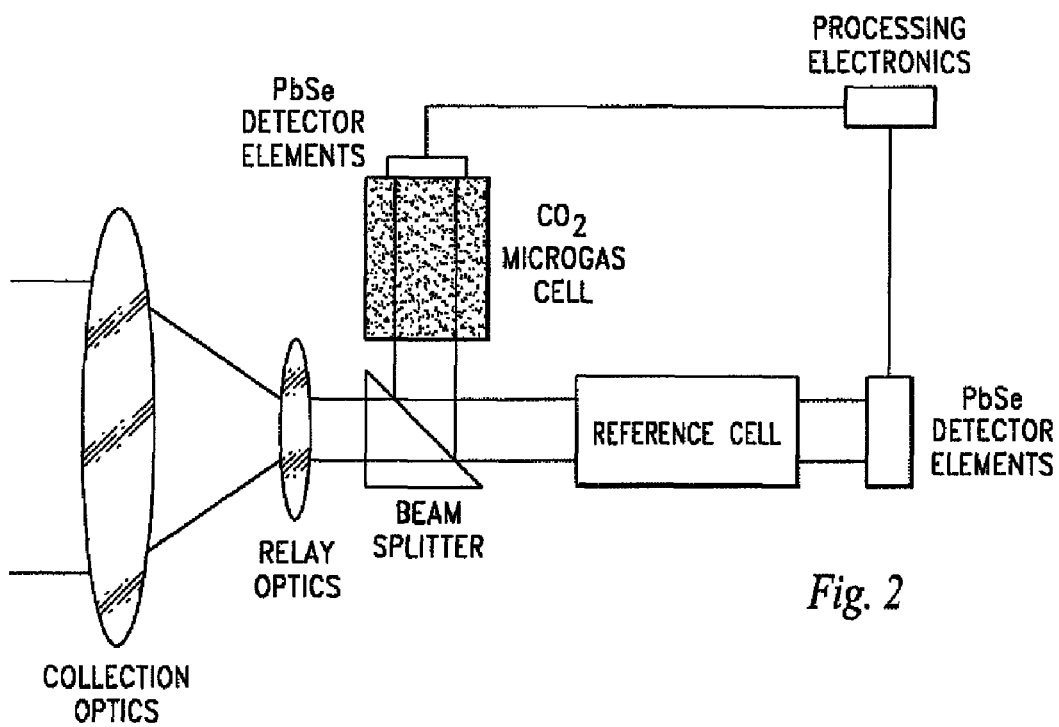
FIG. 2 is a block diagram of an alternative preferred embodiment of the invention for the detection of $CO_2$.

As illustrated in the embodiment of FIG. 2, beam splitting means such as beam splitting optics may be provided to direct a first portion of the collected electromagnetic energy to a reference micro gas cell and to direct a second portion of the collected electromagnetic energy to one or more micro gas cells filled with predetermined gases wherein the plurality of micro gas cells may be scanned using optical scanning means 10 of FIG. 1.

Optical scanning means 10, such as a tip/tilt mirror system, scans the collimated beam upon and into the array of selected micro gas cells 20 which may include a reference micro gas cell.

Radiation collected from the scene is passed through one or more micro gas cells 20 in an array of micro gas cells 15, before being received by one or more detector elements 40.

The electromagnetic energy passing though the spectrally inert reference cell will generate a relatively high detector element output signal from the related detector element 40 due to the fact minimal electromagnetic energy is absorbed thereby (no energy absorption/filter effect).

On the other hand, electromagnetic energy passing through a micro gas cell 20 having the same gas therein as that in the scene of interest will have maximum energy absorption occur and generate a much lower detector element output.

By comparing the ratio of the detector outputs of the reference cells with those of the micro gas cells having the gas of interest therein and though mathematical algorithms executed in electronic processing circuitry 45, (such as a field programmable gate array or equivalent means) the gas "plume" in the field of view can readily and reliably be identified.

Figure 3:
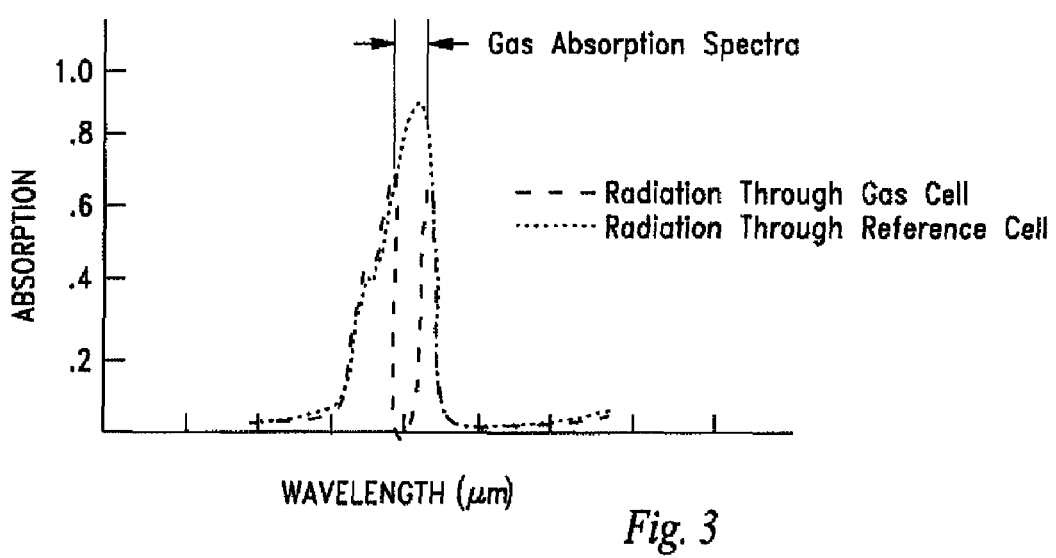
FIG. 3 shows a graph illustrating energy absorption versus wavelength of an optical signal passing through a gas cell versus through a reference cell of the invention.

By way of example and not by limitation, a preferred embodiment of the invention is discussed below and is reflected in FIGS. 2, 3 and 4, in this instance for the detection of $CO_2$ using micro gas cells for remote optical detection of a gas "plume". Although $CO_2$ is not a hazardous gas, the ability to detect $CO_2$ may be used for identifying signs of life, i.e., signs of respiration in for instance, a wounded soldier on a battlefield.

With respect to the above referenced illustrated embodiment, the initial calculation of the micro gas cell size at normal atmospheric pressure results in a cell length of about four cm. This dimension is not desirable for micro gas cell array concept. However, the micro gas cell length scales approximately with the pressure in the cell, hence increasing the internal pressure to, for instance, four times the atmosphere provides substantially similar energy absorption as in a micro cell length of four mm.

A larger detection distance may be achieved by using longer and/or higher pressure within the micro gas cells. Depending on day or night operation, different types of detectors may also be selected. By way of example and not by limitation, two alternative preferred embodiments for day and night operation for a single-micro gas cell system are described.

The $CO_2$ content in an exhaled human breath "plume" is about 4% concentration by volume, compared with ambient air concentration of about 0.04%. Respiration rate is monitored by measuring exhaled $CO_2$ concentration as an additive signal to the path with ambient $CO_2$ concentration.

As earlier discussed, one of the challenges in designing optical filters is maintaining the filter's performance over the wide environmental conditions. Unlike active systems with electronic compensation capabilities, passive systems must rely on self-cancellation methodology to operate reliably over the wide temperature and humidity ranges. In the disclosed invention, by placing the $CO_2$ gas micro gas cell in front of the detectors, all electromagnetic signals will pass through the $CO_2$ disposed within the micro gas cell volume, except for the wavelengths corresponding to the energy absorption bands of the $CO_2$. Thus, detection of the $CO_2$ is achieved by selecting detectors that respond to wavelengths in the relevant absorption bands.

FIG. 2 illustrates schematically the energy absorbed from the electromagnetic signal passing through a micro gas cell having $CO_2$ therein as compared to passing through a reference (empty) cell. The amount of energy absorbed by the respective micro gas cells will be different; hence the output of the detectors receiving the output energy will be different.

Figure 4:
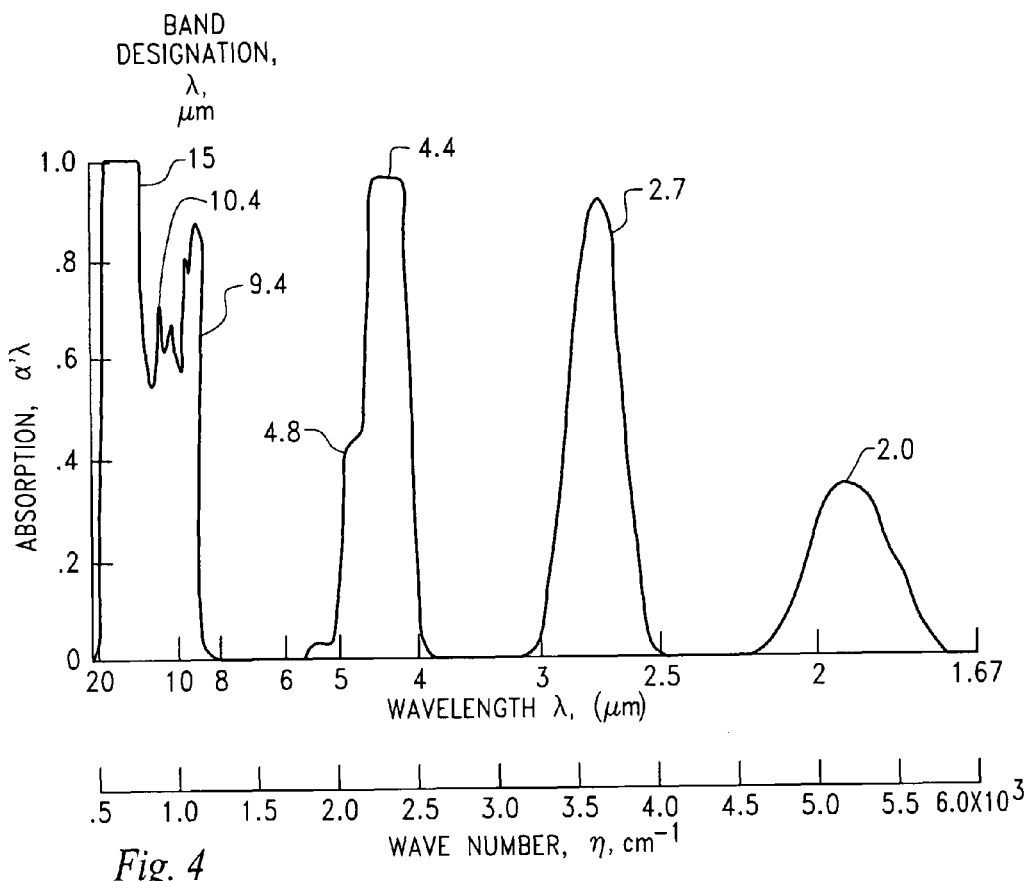
FIG. 4 shows the $CO_2$ spectral absorption bands using a 38.8 mm. micro gas cell of the invention.

As shown in FIG. 4, $CO_2$ has multiple absorption bands in the short wave (SW), mid-wave (MW), and long wave (LW) infrared (LR) portion of the spectra.

The disclosed method for $CO_2$ detection utilizes the 4.3 micron band (MWIR) for day time operation and the 8-12 micron band (LWIR) for night time operation. Detection of the MWIR in this instance depends in part on reflected natural or artificial light, similar to the operation of image intensifier night vision goggles. On the other hand, LWIR is emitted by the source due to its temperature; hence no external lighting is needed. Both bands are selected to minimize interferences from water vapor. FIG. 4 illustrates the energy absorption bands for $CO_2$ using a gas cell of about four cm in length.

The radiance expression for the collected radiation in the wavelength band $\lambda_1,\lambda_2$ is described as follows:

$$L = B(T_{bkgd}; \lambda_1, \lambda_2)\epsilon_{bkgd} + B(T_{sky}; \lambda_1 \lambda_2)\epsilon_{sky}\rho_{bkgd}$$

where the first term is the emitted radiation from the wounded soldier and/or other background near the wounded soldier. The second term represents all external sources of emission such as the sky or nearby objects that may be reflected into the sensor field-of-view. Here it is assumed that transmission and radiance of the atmosphere between the detector and surface are insignificant (short stand-off distance of 30 meters). The equation's terms are defined as:

B(T; $\lambda_1,\lambda$) is the Planck blackbody radiance at temperature T, integrated over the wavelength band $\lambda_1$ to $\lambda_2$ $\rho$ is reflectance and $\epsilon$ is emissivity, sky is the aggregate of emission from surrounding materials including the sky, walls, and objects, and, bkgd is the wounded soldier and/or any immediate objects next to the soldier.

All terms are spectrally variable and the reflection here is the bidirectional reflectance (BDR) which is dependant on angle of incidence and azimuth of the sensor relative to the incoming source.

An analysis has been performed on the amount of collected radiation based on the equation above and the amount of $CO_2$ along the line of sight for a preferred embodiment of the device. The approach taken in the analysis is to minimize the required length of the gas cell while ensuring that variation of the signal intensity between the two paths is within the sensitivity limit of the detector. A design analysis yields a micro gas cell length of approximately four cm, with the gas contained therein of about one atmospheric pressure. A micro gas cell with higher pressure will increase detection range.

The result is such that the detector output signal level changes by about 30% in the proximity of a person exhaling as compared to the normal $CO_2$ concentration in ambient air. Per the above calculation, a micro gas cell can suitably detect the presence of $CO_2$ at distances up to 30 meters.

Turning back to FIG. 2, illustrating an alternative embodiment for a single gas cell system for $CO_2$ intended for day time operation, this embodiment is based on MWIR or the 4.3 micron wavelength band. The scene radiance is first collected, then split into two paths such as by a beam splitter: one path has a $CO_2$ absorption micro gas cell which functions as a $CO_2$ spectral filter, and the other path is spectrally inert as shown.

In this embodiment, the detector is preferably a Lead Selenide (PbSe) detector array responsive to the 4.3 micron wavelength and produces an electrical signal output that is proportional to the intensity of the radiance thereon. The level of $CO_2$ integrated along the optical path length is determined by calculating the ratio of the detected electromagnetic intensity of the light along the two paths.

The illustration of FIG. 2 reflects a single gas cell system embodiment for day time detection of $CO_2$ comprising a Lead Selenide (PbSe) detector responsive to the MWIR absorption band (4.3 microns) of the $CO_2$. The concentration of the gas is determined by calculating the ratio of the intensity of the signals from the two detectors. In this embodiment, it is assumed there is a front end objective lens of 2.5 cm. and the gas cell has a length of four cm.

For night time operation, a second approach utilizing the LWIR wavelengths is more suitable. The night time micro gas cell system uses the capability of the LWIR detectors or imagers (often referred to as Focal Plane Arrays, or FPAs) designed for thermal imaging in the electromagnetic wavelength band of about eight to 12 microns for detecting $CO_2$ gas. The LWIR system may use a configuration is similar to that shown in FIG. 2, but replaces the PbSe detectors with, for instance, a split FPA.

In this embodiment, the $CO_2$ micro gas cell would cover a part of the FPA, while the other part of the FPA receives radiation directly without $CO_2$ filtering. The two images are then compared and their ratio is determined. As in the case of MWIR, the length of the micro gas cell selected in this embodiment is about four cm.

Figure 5:
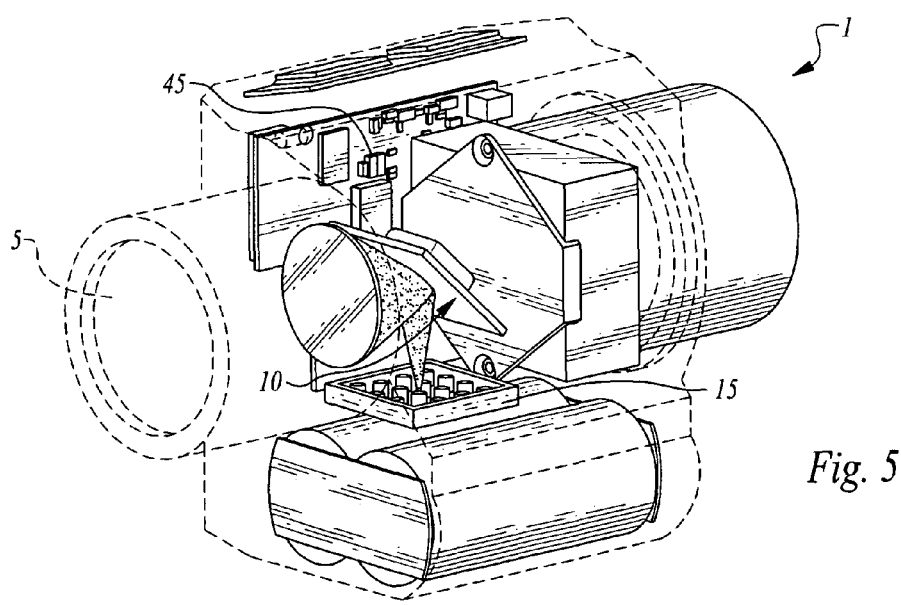
FIG. 5 shows an alternative preferred embodiment of the invention in a hand held viewer configuration.

FIG. 5 shows a preferred embodiment of a gas detection system using the invention that is small enough to be mounted on night vision goggle and binocular. The tube-shape element contains the collection optics 5 and the micro gas cell array 15. The adjacent element is a small battery. An audio signal may be provided to alert the user detection of $CO_2$ and its rate of change. The largest element in the system is the four cm gas cell.

Many alterations and modifications of the above micro gas cell array sensor system 1 may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Although elements may be described above as acting in certain combinations and even initially claimed as such, it is to be expressly understood that one or more elements from a claimed combination can in some cases be excised from the combination and that the claimed combination may be directed to a subcombination or variation of a subcombination. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

We claim:

1. A sensor system comprising:
a structure comprising a plurality of sealed gas volumes having a predetermined gas disposed therein and defining an optical path there through,
a micro lens disposed along the optical path defined by at least one of the sealed gas volumes, and,
optical scanning means for scanning a beam into at least one of the sealed gas volumes.

2. The sensor system of claim 1 wherein at least one of the predetermined gases is disposed within one of the sealed gas volumes at a pressure greater than one atmosphere.

3. The sensor system of claim 1 wherein at least one of the sealed gas volumes comprises a spectrally inert gas therein.

4. The sensor system of claim 1 wherein at least one of the sealed gas volumes comprises at least a partial vacuum therein.

5. The sensor system of claim 1 wherein the predetermined gases in at least two of the sealed gas volumes are substantially identical.

6. The sensor system of claim 1 further comprising:
collection optics means, a detector element having an electronic output, and,
processing electronics for the processing of the electronic output.

7. The sensor system of claim 1 further comprising:
collection optics means, optical scanning means, a photon detector array comprising a plurality of detector elements having an electronic output, and,
processing electronics for the processing of the electronic output.

8. The sensor system of claim 7 further comprising beam splitting means.

9. The sensor system of claim 7 wherein at least one of the predetermined gases comprises $CO_2$.

10. The sensor system of claim 7 wherein at least one of the predetermined gases comprises CO.

11. The sensor system of claim 7 wherein at least one of the predetermined gases comprises $H_2S$.

12. The sensor system of claim 7 wherein at least one of the predetermined gases comprises $N_2O$.

13. The sensor system of claim 7 wherein at least one of the predetermined gases comprises $SO_2$.

14. The sensor system of claim 7 wherein at least one of the sealed gas volumes has a hydrocarbon therein.

15. A method for identifying a gas comprised of the steps of:
collecting electromagnetic radiation emitted or reflected from a scene,
directing at least a first portion of the electromagnetic radiation through a micro lens and through a first micro gas cell having a predetermined gas therein,
directing at least a second portion of the electromagnetic radiation through a micro lens and through a second micro gas cell,
receiving the first portion of electromagnetic energy upon a first detector element having a first detector output,
receiving the second portion of electromagnetic energy upon a second detector element having a second detector output, and,
comparing the first detector output to the second detector output to define a ratio between the first detector output and the second detector output.

16. The method of claim 15 wherein the directing of the first portion of the electromagnetic energy or the second portion of the electromagnetic energy comprises the use of beam splitting means.

17. The method of claim 15 wherein the directing of the first portion of the electromagnetic energy or the second portion of the electromagnetic energy comprises the use of optical scanning means.

* * * * *